United States Patent [19]

Jackson et al.

[11] Patent Number: 4,724,855
[45] Date of Patent: Feb. 16, 1988

[54] DENTURE POWER WASHER

[76] Inventors: Albert P. Jackson, 3660 Grand Ave., Des Moines, Iowa 50312; John E. Gilbertson, 3209 Douglas, Des Moines, Iowa 50313

[21] Appl. No.: 901,817

[22] Filed: Aug. 29, 1986

[51] Int. Cl.⁴ ............................................. B08B 3/04
[52] U.S. Cl. ..................... 134/93; 134/182; 134/201; 206/83; 215/1 C; 215/6; 220/23
[58] Field of Search ............ 134/93, 117, 137, 151, 134/154, 155, 182, 198, 200, 201; 68/213, 214; 366/130; 422/261; 206/83; 220/23; 215/1 C, 6

[56] References Cited

U.S. PATENT DOCUMENTS

| | | | |
|---|---|---|---|
| 2,160,328 | 5/1939 | Durham | 68/214 |
| 2,659,380 | 11/1953 | Jackson | 134/182 X |
| 2,941,689 | 6/1960 | Black | 215/6 X |
| 3,009,468 | 11/1961 | Eberle | 134/199 X |
| 3,098,496 | 7/1963 | Milbourne | 134/199 X |
| 3,586,012 | 6/1971 | Paule | 134/93 |
| 3,923,178 | 12/1975 | Welker, III | 215/1 C |

*Primary Examiner*—Philip R. Coe
*Attorney, Agent, or Firm*—James D. Birkenholz

[57] ABSTRACT

A method for use and application comprising a power denture washer having a washing container for housing the denture with a removable sealable lid. Disposed within the lid is a denture cleaner storage compartment with a removable sealable top cover. Disposed in the bottom of the washing container is a drain. The methodology includes placement of the denture within the container, rinsing under flowing water, adding the denture cleanser matter, inverting and filling with water and letting the denture soak and inverting the washing container to drain the liquid out and rinsing the denture under a stream of water.

3 Claims, 8 Drawing Figures

DENTURE POWER WASHER

BACKGROUND OF THE INVENTION

1. Field of the Invention

The present invention relates generally to dental equipment and more particularly to an apparatus and methodology for the cleansing of dentures and the storing of denture cleansing material.

2. Background of the Invention

The art of denture cleaning equipment and methodology typically includes a container into which the denture is placed along with a denture cleaning material and the denture left to soak. The dentures are then hand removed and washed off and thereafter reused. Typically these include various devices to hold the denture in place and necessitating a shaking action of the container to coat the denture with the cleansing liquid. Examples include U.S. Pat. No. 2,102,643 to Pellegrini, U.S. Pat. Nos. 2,568,838 2,565,899 to Wilcox, U.S. Pat. No. 2,122,583 to Parizot and U.S. Pat. No. 2,714,443 to Kuvin. Other references illustrating means for the cleansing include U.S. Pat. No. 2,443,988 to Morse, U.S. Pat. No. 2,163,862 to Wing and U.S. Pat. No. 3,133,305. The art does not provide equipment for the effective cleansing of dentures either by providing a prewashing wherein full effective circulation of water passes over the denture. Further the art does not adequately provide for drainage of the container and frequently necessitates physically handling of the dentures during the washing process. Also the art does not provide for convenient storage and access to the denture cleansing material in association with the denture cleansing equipment.

Therefore, there is a need for a compact convenient denture washing apparatus which by design and operation effectively and efficiently cleans dentures and provides a means for the storage of denture cleansing material.

SUMMARY OF THE INVENTION

A power denture washer apparatus and method of using the same for cleansing dentures including a washing container for receiving dentures having four walls and a bottom with a lid threadably and sealingly attached the walls. A drain hole extends through the bottom for removal of liquids within the washing container. One pair of opposing walls are concaved and the other pair of opposing walls are convex. A denture cleanser storage compartment extending through and sealingly attached to the lid, having a side wall communicating with a bottom for storage of denture cleansing material. A top cover is threadably received by the side wall. The methodology includes removal of the lid and placement of the dentures in the washing container and rinsing the dentures under a stream of water. A predetermined amount of denture cleansing material is removed for the denture cleanser storage compartment and deposited within the washing container and the lid is replaced on the washing container. The washing container is inverted and filled through the drain with a predetermined amount of water. The washing container sets for a predetermined amount of time to allow the chemical to work upon the dentures, thereafter the washing container is uprighted and the liquid drained off. The lid is removed and the final rinsing of the dentures under a stream of water occurs.

DESCRIPTION OF THE PREFERRED EMBODIMENT

Figure 1:
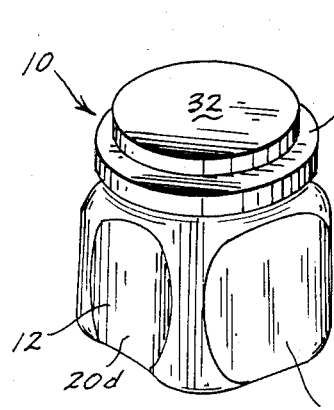
FIG. 1 is a perspective view of the Power Denture Washer of the present invention.
Figure 2:
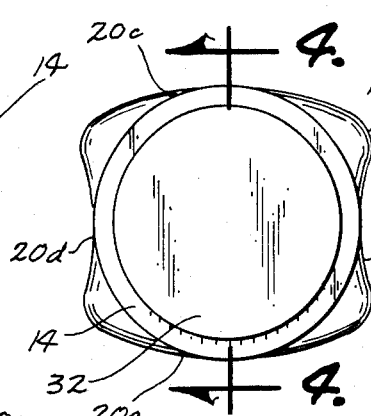
FIG. 2 is a top view of the Power Denture Washer.
Figure 3:
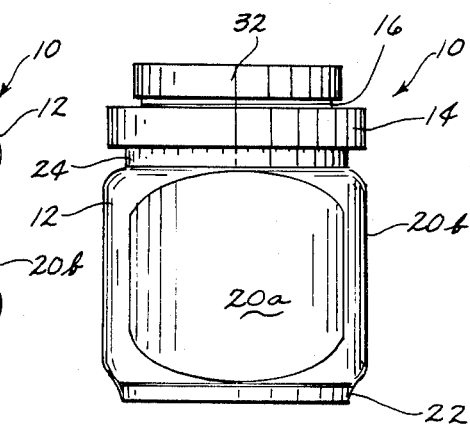
FIG. 3 is a side view of the Power Denture Washer.
Figure 4:
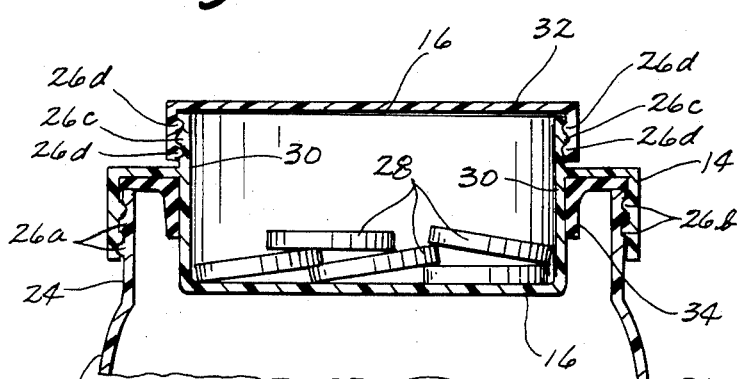
FIG. 4 is a partial cross-sectional view taken along lines 4—4 of FIG. 2 illustrating the denture cleansing material.

Referring now to the drawings wherein like reference numerials designate identical or corresponding parts throughout the several views, the power denture washer of the present invention is illustrated generally at 10 in FIG. 1.

Generally, the power denture washer 10 (FIGS. 1-5 and 6) includes a washer container 12, a lid 14, a denture cleanser storage compartment 16 and a drain 18.

Specifically, the washing container 12 (FIGS. 1-5) includes a rectangular container having four walls 20a, 20b, 20c and 20d communicating with a bottom 22 at their lower end and joining together to form a collar 24 at their upper portion. The configuration of the meeting surfaces of the walls 20a-d and the bottom 22 provide a rounded curved surface which directs the water flowing into the container 12 and striking the bottom to swirl around the container to enhance the cleansing action.

The bottom 22 includes the drain 18 which is an aperture extending through the center of the bottom 22. The collar 24 is formed from the joining of the sides 20a-d and extends upwards from above the sides 20a-d and includes threads 26a. The threads 26a mate up to threads 26b on the lid 14 wherein the lid 14 is secured on the collar 24. Disposed within the lid 14, the denture cleanser storage compartment 16 extends through the lid 14 to form a holding area for denture cleanser chemical 28 which for illustration purposes is shown in tablet form which conforms to the usual mode of the chemical. The upper region of the walls 30 of the compartment 16 include threads 26c. The threads 26c mate up to threads 26d on cover 32 of the compartment 16a to secure the cover 32 on the compartment 16. A gasket 34 extends around the mating surfaces of the wall 30, the lid 14 and the collar 24 of the container 12. The gasket 34 generally is formed from pliable material to allow the lid 14 to be tightened down on the container 12 making a liquid tight seal between the container 12 and lid 14.

The walls 20a-d are sloped to further enhance the cleansing process by contributing to the swirling action of water flowing into and about the container 12. The opposing sides 20a and 20c are convex in configuration and the opposing sides 20b and 20d are concave in configuration. These shapes also facilitate handling and griping of the power denture washer 10.

Figure 5:
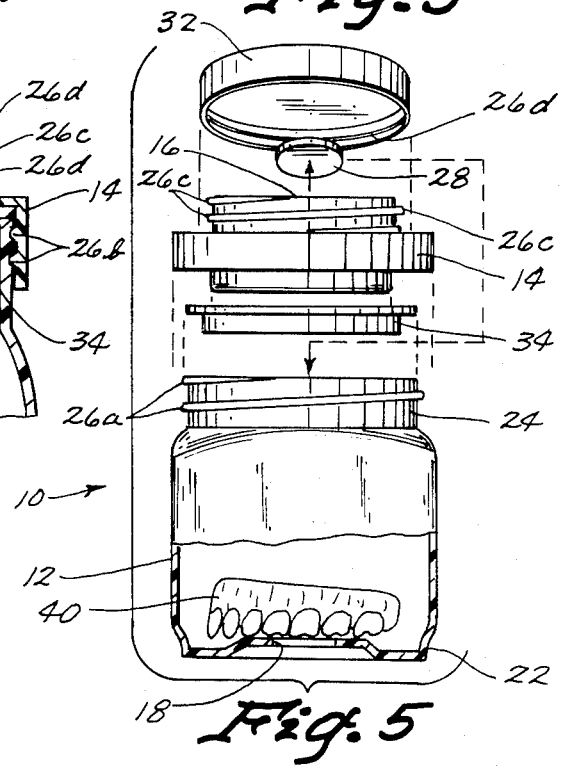
FIG. 5 is a side cross-sectional exploded view illustrating removal of the denture cleansing material and placement of it within the washing container and illustrating a denture resting on the bottom of the washing container.
Figure 6:
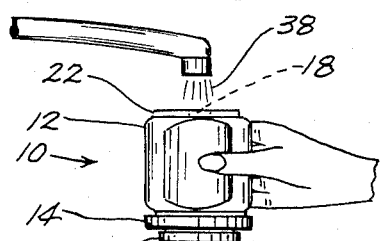
FIG. 6 is a side view illustrating filling the washing container with water from a conventional water faucet.
Figure 8:
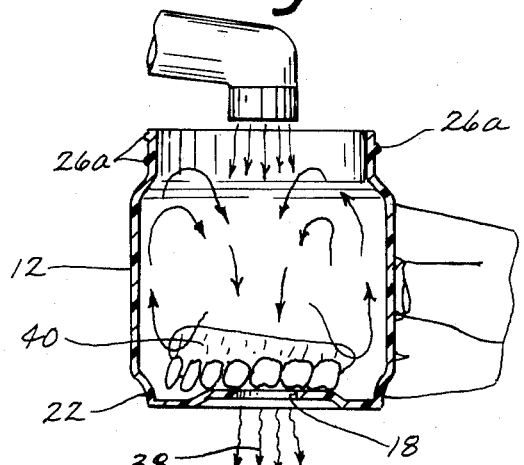
FIG. 8 is a side view illustrating rinsing of the dentures under a conventional water faucet.
Figure 7:
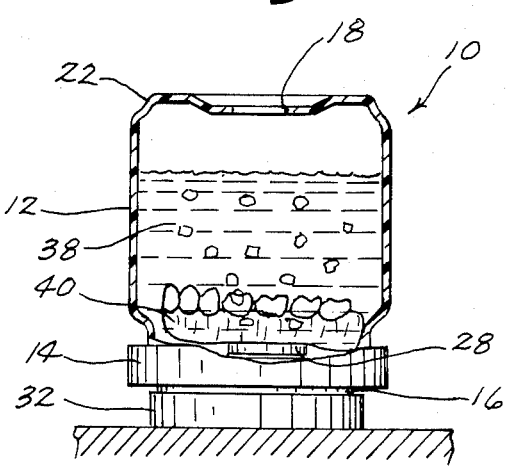
FIG. 7 is a partial cross-sectional view illustrating the washing container inverted, filled with water and the cleansing chemical with debris being removed from the dentures.

During usage of the power denture washer 10, the lid 14 is removed and the denture 40 placed inside the container 12 (FIGS. 5-7) and the denture washer 10 placed under a water faucet 36 with water 38 flowing into the container 12 (FIG. 8) to initially wash off the denture 40. The water movement around the inside of the container is accented by the curvature of the walls 20a-d and their junction with the bottom 22 and the collar 24 to provide an enhanced washing action. The accumulated water 38 within the container 12 ultimately flows out the drain 18. Upon completion of the rinsing, the cover 32 is removed from the denture cleanser storage compartment 16 and the chemical 28 is deposited into the washing container 12 (FIG. 5). The lid 14 and cover 32 are reapplied and the denture washer 10 is inverted and filled to a given level with water (FIG. 6) through the drain 18. The denture washer 10 is left inverted to permit the chemical 28 to work on the dentures 40 (FIG. 7) with the debris 42 being removed. After soaking, the denture washer 10 is held right side up, the lid 14 is removed and the dentures 40 are rinsed under flowing water 38 (FIG. 8) and the washing cycle is complete. Applicant's power denture washer 10 provides a self contained unit which provides means for storing the denture washer which is compact, simple to use with enhanced water flow within the denture washer 10 providing significantly improved cleansing action on the dentures 40.

It is to be understood that the invention may be practiced otherwise than as specifically set forth in the preferred embodiment and still fall within the scope of the appended claims.

I claim:

1. A Power Denture Washer for the cleaning of dentures comprising:

a washer container for receiving dentures, the washer container having four sides and a bottom in communication with each other and a lid, the lid being threadably removable from and overlying the sides and sealingly attached to the sides at a collar, the collar forming the top of the sides and including a threaded portion which receives the lid; respective regions formed from interior meeting surfaces of the sides and the bottom which communicate and of the sides and the collar which communicate providing rounded curved surfaces permitting the smooth flow of a liquid within the container; a drain, the drain forming an aperture extending through the bottom through which liquid within the container may pass;

a denture cleanser storage compartment for receiving denture cleansing material received within the lid and sealingly attached thereto, the compartment having a wall communicating with a bottom and a top cover overlying the wall and removably attached thereto.

2. A power denture washer as claimed in claim 1 wherein two of the opposing walls of the washing container are concave.

3. A power denture washer as claimed in claim 2 wherein the other two of the opposing walls are convex.

* * * * *